United States Patent [19]

Ishii et al.

[11] Patent Number: 4,908,454
[45] Date of Patent: Mar. 13, 1990

[54] PROCESS OF PRODUCING GUANIDINOTHIAZOLE DERIVATIVES

[75] Inventors: Yoshio Ishii, Saitama; Isao Yanagisawa, Tokyo, both of Japan

[73] Assignee: Yamanouchi Pharmaceutical Co., Ltd., Chuo-Tokyo, Japan

[21] Appl. No.: 300,760

[22] Filed: Jan. 23, 1989

Related U.S. Application Data

[60] Continuation of Ser. No. 105,454, Oct. 2, 1987, abandoned, which is a division of Ser. No. 766,634, Aug. 16, 1985, abandoned.

[30] Foreign Application Priority Data

Aug. 30, 1984 [JP] Japan .................. 59-182129

[51] Int. Cl.$^4$ ............................................. C07D 277/48
[52] U.S. Cl. ........................................ 548/193; 548/197
[58] Field of Search ................................. 548/193, 197

[56] References Cited

U.S. PATENT DOCUMENTS

| | | | |
|---|---|---|---|
| 3,174,997 | 3/1965 | Campbell | 548/378 |
| 3,203,988 | 8/1965 | Campbell | 564/230 |
| 3,246,031 | 4/1966 | Campbell | 564/237 |
| 3,248,426 | 4/1986 | Dvornik | 564/237 |
| 3,444,165 | 5/1969 | Pollak et al. | 548/378 |
| 3,456,009 | 7/1969 | Green | 564/237 |
| 3,681,459 | 8/1972 | Hughes | 564/238 |
| 3,903,159 | 9/1975 | Hughes et al. | 514/930 |
| 3,947,455 | 3/1976 | Hughes et al. | 514/930 |
| 4,000,279 | 12/1976 | Hughes et al. | 514/310 |
| 4,025,652 | 5/1977 | Diamond | 564/238 |
| 4,088,769 | 5/1978 | Black | 514/365 |
| 4,283,408 | 8/1981 | Hirata et al. | 548/193 |
| 4,347,370 | 8/1982 | Gilman | 548/193 |
| 4,362,736 | 12/1982 | Hirata et al. | 548/193 |
| 4,451,463 | 5/1984 | Larse | 548/193 |
| 4,570,000 | 2/1986 | Jone | 548/193 |

OTHER PUBLICATIONS

March, Advanced Organic Chemistry, p. 803 (1985).
Migridichian, Organic Cyanogen Compounds, pp. 66-67 (1947).

Primary Examiner—Robert Gerstl
Attorney, Agent, or Firm—Burgess, Ryan & Wayne

[57] ABSTRACT

A process is provided for producing a guanidinothiazole compound represented by the formula:

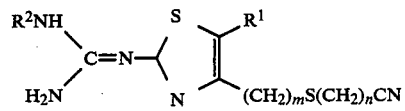

wherein, $R^1$ and $R^2$, which may be the same or different, each represents a hydrogen or an alkyl group having 1 to 3 carbon atoms; m represents 1 or 2; and n represents 2, 3 or 4. The process comprises reacting an aminothiazole compound of the formula:

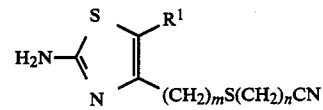

with a cyanamide or an amidinopyrazole, the compounds are useful as intermediates in the preparation of a gastric acid secretion inhibitor.

4 Claims, No Drawings

PROCESS OF PRODUCING GUANIDINOTHIAZOLE DERIVATIVES

This is a continuation of application Ser. No. 105,454, filed 10-2-87 which is a division of application Serial No. 766,634, filed Aug. 16, 1985, both now abandoned.

FIELD OF THE INVENTION

This invention relates to a process of producing guanidinothiazole derivatives or acid addition salts thereof. More particularly, the invention relates to a process of producing a guanidinothiazole derivative represented by the general formula (I)

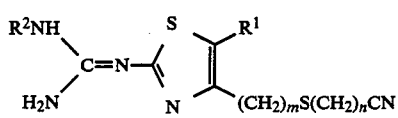

wherein, $R^1$ and $R^2$, which may be the same or different, each represents a hydrogen atom or an alkyl group having 1 to 3 carbon atoms; m represents 1 or 2; and n represents 2, 3, or 4 or acid addition salts thereof.

The compound of general formula (I) obtained by the process of this invention is an intermediate compound for producing guanidinothiazole series compounds. For example, by treating the compound of general formula (I) with absolute methanol to form methyl[3-(2-ganidinothiazol-4-yl)methylthio]propion imidate and reacting the product with sulfamide, the compound can be induced into famotidine useful as a gastric acid secretion inhibitor.

BACKGROUND OF THE INVENTION

As a process of producing the compound shown by general formula (I), there is known the process shown by the following reaction formulae (Japanese Patent Publication (Unexamined) No. 46,873/'81):

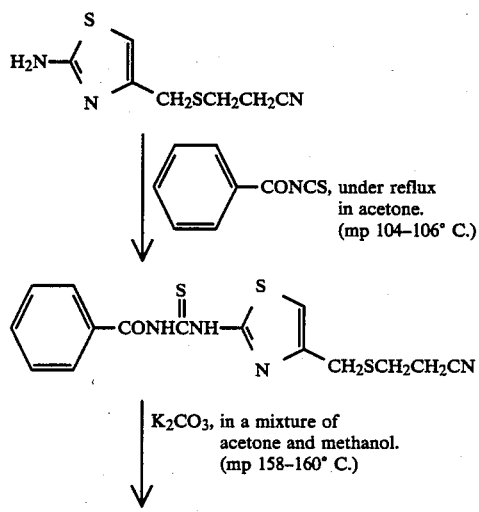

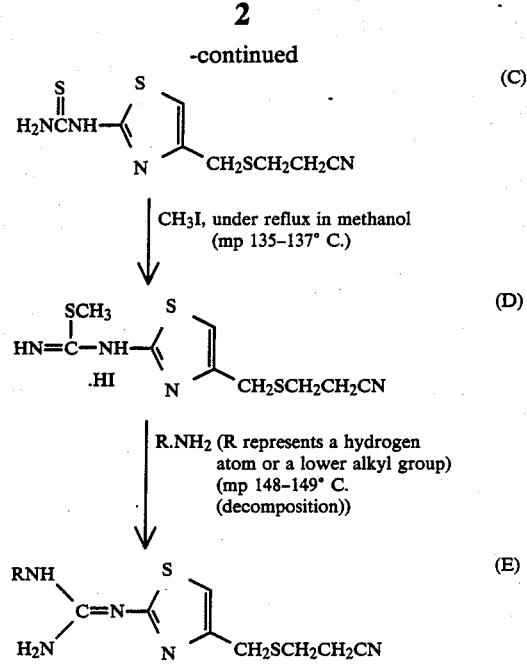

However, this process comprises many steps, one requires much time, and hence the process is unsuitable for industrial practice.

SUMMARY OF THE INVENTION

The object of this invention is to provide a process of producing the compound shown by general formula (I) and acid-addition salts thereof without the above-described difficulties in the conventional process.

As the results of various investigations from the view point of the reduction of working steps and simplification of the production process of the compound, the inventors have discovered that the object of this invention can be attained by the process of this invention as set forth hereinbelow.

That is, according to this invention, there is provided a process of producing a guanidinothiazole derivative represented by the general formula (I)

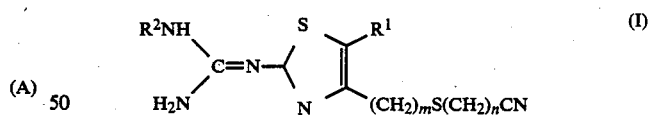

wherein, $R^1$ and $R^2$, which may be the same or different, each represents a hydrogen or an alkyl group having 1 to 3 carbon atoms; m represents 1 or 2; and n represents 2, 3, or 4 or an acid addition salt thereof, which comprises reacting an aminothiazole derivative represented by the general formula (II)

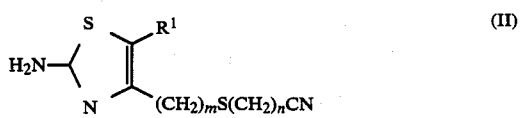

wherein, $R^1$, m and n have the same significance as defined above or an acid addition salt thereof and a cyanamide derivative represented by the general formula ($III_1$)

$R^2NHCN$ (III₁)

wherein, $R^2$ has the same signifance as defined above or an amidinopyrazole derivative represented by general formula (III₂)

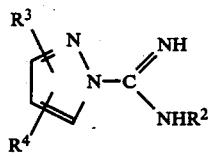

(III₂)

wherein, $R^3$ and $R^4$, which may be the same or different, each represents a hydrogen atom or an alkyl group having 1 to 3 carbon atoms and $R^2$ has the same significance as defined above or an acid addition salt thereof.

DESCRIPTION OF THE PREFERRED EMBODIMENT

In the general formulae described above, the alkyl group of 1 to 3 carbon atoms includes a methyl group, an ethyl group, a propyl group, and an isopropyl group and the acid addition salts of the compounds shown by general formulae (I), (II) and (III₂) include mineral acid salts such as hydrochlorides, sulfates, etc., of these compounds.

The process of this invention is performed as follows.

The reaction of the compound of the general formula (II) or an acid addition salt thereof and the cyanamide derivative shown by the formula (III₁) is performed by reacting both compounds in a proper organic solvent under heating. In this case, when the cyanamide derivative shown by the general formula (III₁) is used in an excessive amount to the amount of the compound (II) or an acid addition salt, a good result is obtained. A suitable solvent which is used for the reaction includes methanol, ethanol, n-buthanol, iso-propanol, methylcellosolve and the like. The reaction is usually performed at about the reflux temperature of the solvent used but can be performed at temperatures higher than or lower than the aforesaid temperature. The reaction is accelerated by the addition of a catalyst. As the catalyst, a Lewis acid is suitable for example, zinc oxide, zinc chloride, copper[I] chloride, aluminum chloride and the like, can be used. The product is isolated from the reaction mixture and purified by extraction using an organic solvent, crystallization, or, if necessary, column chromatography.

Then, the reaction of the compound of formula (II) or an acid addition salt thereof and the amidinopyrazole derivative shown by the formula (III₂) is performed by directly heating these compound without using solvent or heating these compounds in a highboiling solvent. As the high-boiling solvent, for example, 1,3-dimethyl-2-imidazolidinone and the like, can be used. As the amidinopyrazole derivative shown by the formula (III₂), there are amidinopyrazoles substituted by an alkyl group having 1 to 3 carbon atoms at the pyrazole ring, such as 3-methylamidinopyrazole, 3,5-dimethylamidinopyrazole and the like, in addition to amidinopyrazole. The amidinopyrazole derivative of formula (III₂) can be supplied to the reaction as an acid addition salt thereof such as a hydrochloride and the like. In addition, the production process of the amidinopyrazole derivative of formula (III₂) or the acid addition salt thereof is reported in "Journal of the American Chemical Society", Vol. 75, 4053(1953). The amount of the amidinopyrazole of formula (III₂) is employed in excess. The amount thereof is usually at least twice the molar amount of the compound shown by formula (II). The reaction is properly performed at 100° C. or temperatures higher than 100° C. The product can be easily isolated by extraction using an organic solvent or recrystallization.

Then, the invention will further be explained more practically by the following examples.

EXAMPLE 1

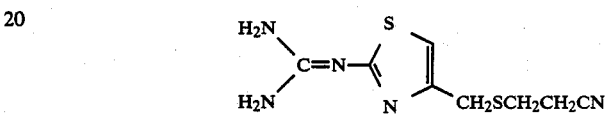

To 6.8 g of 3-(2-aminothiazol-4-ylmethylthio)-propionitrile was added 80 ml of isopropanol and while stirring the mixture, 1.3 g of hydrogen chloride gas was introduced into the mixture. Then, after adding thereto 0.8 g of zinc oxide and 8 g of cyanamide, the mixture was refluxed for 24 hours. Furthermore, the operation of adding 8 g of cyanamide to the mixture followed by refluxing for 24 hours was repeated twice. After cooling, 150 ml of methanol was added to the reaction mixture thus obtained, insoluble matters were filtered away, and the filtrate then formed was evaporated under reduced pressure. To the residue formed were added 35 ml of methanol and 180 ml of water, and then after further adding thereto 5 g of anhydrous potassium carbonate with stirring, the product was extracted using a mixture of chloroform and methanol (4:1). The organic layers formed were collected, concentrated under reduced pressure, and the residue thus formed was separated using silica gel column chromatography and concentrated. The residue thus formed was crystallized in a mixture of water and isopropanol and recovered by filtration to provide 3.8 g of 3-(2-guanidinothiazol-4-ylmethylthio)propionitrile having a melting point of 129° to 130° C.

EXAMPLES 2 to 13

By following almost the same procedure as in Example 1 using the solvents and catalysts as shown in the following table, the same compound as Example 1 was obtained.

In the above reaction, the reaction was performed under refluxing.

| Example | Reaction solvent | Catalyst | Amount of cyanamide |
|---|---|---|---|
| 2 | Isopropanol | ZnF₂ (catalytic amount) | 16 mole times |
| 3 | " | ZnCl₂ (catalytic amount) | " |
| 4 | " | ZnI₂ (catalytic amount) | " |
| 5 | " | ZnO (catalytic amount) | " |
| 6 | Methanol | ZnCl₂ (0.3 mole) | " |
| 7 | Ethanol | ZnCl₂ (0.3 mole) | " |
| 8 | n-Butanol | ZnCl₂ (0.3 mole) | " |

-continued

| Example | Reaction solvent | Catalyst | Amount of cyanamide |
|---|---|---|---|
| 9 | Methylcellosolve | $ZnCl_2$ (0.3 mole) | " |
| 10 | Methanol | ZnO (0.3 mole) | " |
| 11 | Ethanol | ZnO (0.3 mole) | " |
| 12 | n-Butanol | ZnO (0.3 mole) | " |
| 13 | Methylcellosolve | ZnO (0.3 mole) | " |

EXAMPLE 14

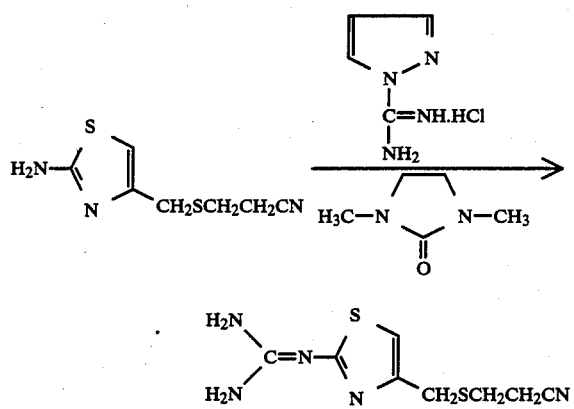

To 5 g of 3-(2-aminothiazol-4-ylmethylthio)propionitrile were added 11 g of amidinopyrazole hydrochloride and 15 ml of 1,3-dimethyl-2- imidazolidinone and the mixture was heated to 110°–120° C. for 4 hours. After cooling, 120 ml of water was added to the reaction mixture and then the product was extracted twice with 50 ml of ethyl acetate and washed. The aqueous layer thus formed was collected, added with 11 g of anhydrous potassium carbonate and 10 ml of isopropanol, the crystals thus formed were collected by filtration to provide 2.33 g of 3-(2-guanidinothiazol-4-ylmethylthio)propionitrile having a melting point of 127°–128° C.

EXAMPLE 15

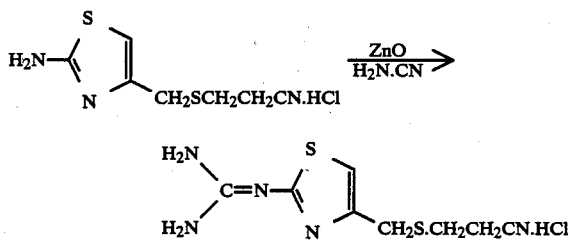

To a mixture of 50 g of 3-(2-aminothiazol-4-ylmethylthio)propionitrile hydrochloride, 50 ml of isopropanol and 5 g of zinc oxide was added 100 g of an aqueous solution of 50 (w/w)% cyanamide and then the mixture was refluxed for 24 hours. 50 g of an aqueous solution of cyanamide was added and refluxing the mixture for 12 hours was repeated twice. The reaction mixture thus obtained was concentrated under reduced pressure, insoluble matters thus precipitated were filtered away, and the filtrate was further concentrated under reduced pressure. Water was added to the residue thus formed and after alkalizing the mixture by adding thereto 30 g of potassium carbonate, the product formed was extracted thrice with ethyl acetate. The organic layer thus formed was collected and washed with a saturated aqueous sodium chloride solution. Then, 25 ml of an ethanol solution of 4.5 N HCl was added to the organic layer, the mixture was cooled with stirring, and crystals thus deposited were collected by filtration to provide 31 g of 3-(2-guanidinothiazol-4-ylmethylthio)propionitrilehydrochloride having melting point of 137 to 140° C.

What is claimed is:

1. A process of producing a guanidinothiazol compound of the formula

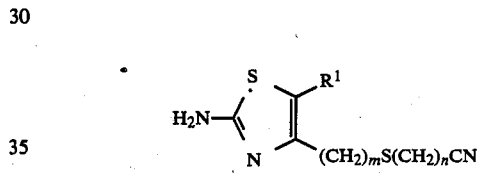

wherein $R^1$ and $R^2$, which may be the same or different, each represents a hydrogen or an alkyl group having 1 to 3 carbon atoms; m represents 1 or 2; and n represents 2, 3 or 4, or an acid addition salt thereof, which comprises reacting in the presence of a Lewis acid catalyst, an aminothiazol compound represented by the formula:

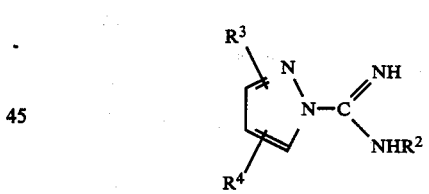

wherein $R^1$, m and n have the same values as defined above, or an acid addition salt and an amidinopyrazole compound represented by the formula:

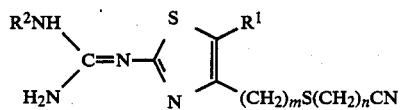

wherein $R^3$ and $R^4$, which may be the same or different, each represents a hydrogen atom or an alkyl group having 1 to 3 carbon atoms and $R^2$ has the same value as defined above, said reaction being effected in a high-boiling solvent at a temperature of at least 100° C. and wherein said Lewis acid catalyst is selected from the group consisting of zinc oxide, zinc chloride, copper (I) chloride and aluminum chloride, and thereafter recovering said guanidinothiazole.

2. The process of claim 1 where said high-boiling solvent is 1,3-dimethyl2-imidazolidinone.

3. The process of claim 1 wherein the mole ratio of amidinopyrazole to aminothiazole is at least 2:1.

4. The process of claim 1 wherein said aminothiazole compound is 3-(2-aminothiazol-4-ylmethylthio) propionitrile or an acid addition salt thereof.

* * * * *